United States Patent
Hielscher

(10) Patent No.: US 6,481,493 B1
(45) Date of Patent: Nov. 19, 2002

(54) ARRANGEMENT FOR HEAT DISCHARGE, PARTICULARLY FOR ULTRASONIC TRANSDUCERS WITH HIGH PERFORMANCE

(75) Inventor: Harald Hielscher, Stahnsdorf (DE)

(73) Assignee: Dr. Heilscher GmbH, Teltow (DE)

( * ) Notice: Subject to any disclaimer, the term of this patent is extended or adjusted under 35 U.S.C. 154(b) by 0 days.

(21) Appl. No.: 09/762,103
(22) PCT Filed: Aug. 2, 1999
(86) PCT No.: PCT/EP99/05535
 § 371 (c)(1),
 (2), (4) Date: Mar. 27, 2001
(87) PCT Pub. No.: WO00/08630
 PCT Pub. Date: Feb. 17, 2000

(30) Foreign Application Priority Data

Aug. 4, 1998 (DE) .......................................... 198 36 229

(51) Int. Cl.$^7$ ................................................ H05K 7/20
(52) U.S. Cl. ...................... 165/169; 165/80.3; 165/185; 361/704
(58) Field of Search .............................. 165/80.2, 80.3, 165/185, 69, 84; 361/704, 710; 174/16.3; 367/165, 173

(56) References Cited

U.S. PATENT DOCUMENTS

| 2,176,657 A | * | 10/1939 | Finch ......................... 165/80.3 |
| 2,313,379 A | * | 3/1943 | Wood ........................... 165/185 |
| 2,507,636 A | * | 5/1950 | Kistler ........................ 165/80.2 |
| 2,529,279 A | * | 11/1950 | Breisch ....................... 165/80.3 |
| 2,799,793 A | * | 7/1957 | De Cain ....................... 165/180 |
| 4,574,879 A | * | 3/1986 | DeGree et al. .............. 165/185 |
| 5,025,666 A | * | 6/1991 | Kobayashi et al. .......... 310/327 |
| 5,038,067 A | * | 8/1991 | Tabin .......................... 310/321 |
| 5,171,387 A | * | 12/1992 | Wuchinich ................ 156/580.1 |
| 5,545,942 A | | 8/1996 | Jaster et al. |
| 5,555,887 A | * | 9/1996 | Fraser et al. ................. 600/472 |

FOREIGN PATENT DOCUMENTS

| DE | 2745010 | 11/1979 | |
| DE | 3528291 A1 | 2/1987 | |
| DE | 4339786 A1 | 5/1996 | |
| EP | A553804 | 8/1993 | |
| EP | A782125 | 7/1997 | |
| JP | 9-129158 A * | 5/1997 | ............ H01J/29/88 |

* cited by examiner

Primary Examiner—Allen Flanigan
(74) Attorney, Agent, or Firm—Birch, Stewart, Kolasch & Birch, LLP

(57) ABSTRACT

The invention relates to a heat dissipating device, especially for high-performance industrial ultrasonic transducers. The aim of the invention is to produce a device that enables high-performance ultrasonic transducers to operate continuously in environments with high heat and/or high humidity, whereby heat is dissipated in an explosion-proof embodiment in a more effective manner. This is achieved by surrounding the ultrasonic transducer (1) with a closed cooling system comprising a layer (2) that absorbs vibrations, e.g. a silicon rubber layer, and a layer that dissipates heat (3), e.g. silica sand.

2 Claims, 1 Drawing Sheet

Schnitt A - A

Schnitt: A - A

Figure 1:
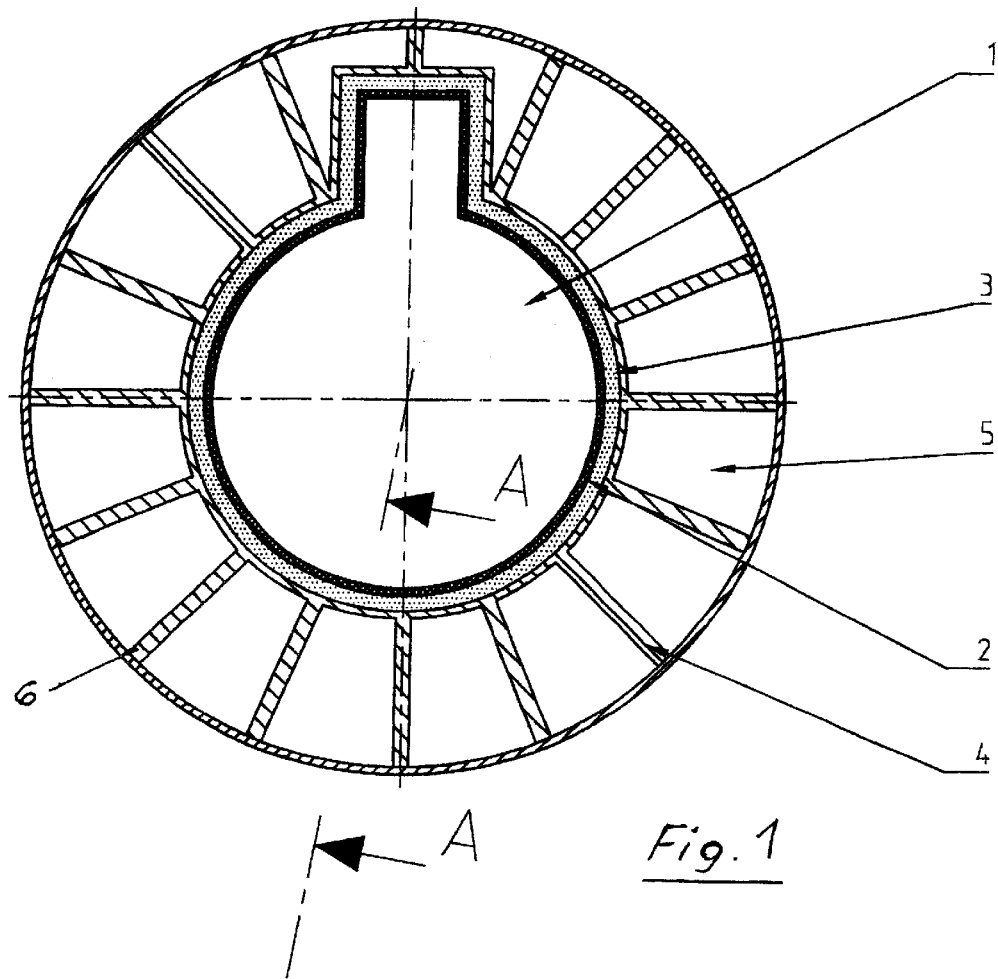

ARRANGEMENT FOR HEAT DISCHARGE, PARTICULARLY FOR ULTRASONIC TRANSDUCERS WITH HIGH PERFORMANCE

This application is the national phase under 35 U.S.C. § 371 of PCT International Application No. PCT/EP99/05535 which has an International filing date of Aug. 2, 1999, which designated the United States of America.

DESCRIPTION

The invention concerns an arrangement for heat discharge, particularly for ultrasonic transducers with high performance rating for the industrial application.

It is generally known to cool ultrasonic transducers with high capacity rating for the purpose of discharging heat which occurs as a result of the conversion of the electric energy into mechanical energy by means of internal friction in the piezoelectric elements and by means of electric losses.

In many cases the known cooling systems consist only of a casing which encloses the ultrasonic transducer, such casing having openings (ports) through which heat is withdrawn by means of convection (prospectus of Messrs Bandelin electronic "Sonorex" Ultrasonic Disintegrators", Sonopuls HD 60). This type of cooling is insufficient for high performance ratings.

With an additional cooling by means of a fan, dust and moisture is transported into the casing and the danger of electric short-circuits caused by bridge formation increases.

The withdrawal of heat by way of a horn-flange-casing-connection mounted at the ultrasonic transducer is also known, where the heat discharge is effected by way of a copper cooling plate for water cooling (prospectus of Messrs TELSONIC "Ultrasonic High Performance Reactor, Series SRR"). In this case also, the heat discharge for high performance ratings and continuous operation is insufficient. In addition to the poor heat conductivity of titanium, and where this arrangement is concerned, only a narrow connection to the horn at the location of a vibration node (zero point) can be realised in order to create a vibration-disengaged transition. With this, there is only a minor heat transfer from the heat source to the cooling system which is not sufficient for the continuous operation at high performance levels. A transfer of vibrations to the cooling system is to be avoided as capacity is lost and a further heat increase would result.

Further numerous variants of the cooling are known where, for example, the casings are provided with air cooling or with high-pressure air. These systems also indicate the danger of electric short-circuit. Closed systems with fans and heat exchange from the inside to the outside are also known. However, these are sophisticated from equipment-technical aspects and allow only a limited heat withdrawal.

In DE 43 39 786 A1 an arrangement for heat discharge is described where, for the purpose of heat discharge of electronic components immediately on the surface of the casing of the electronic component a heat-conductive plastic form body made from a silicone polymer is envisaged which has a surface contact with the casing that also serves cooling purposes.

In DE 35 28 291 A1 an arrangement is stated for the cooling of electronic structural elements where bulk material takes over the heat transfer from the components to the cooling bodies. Sand or glass pearls having a certain grain sizing are envisaged as a bulk material.

These arrangements also require a sophisticated cooing system with cooling bodies, and have the disadvantages associated with these.

A disadvantageous factor with all known solutions is the fact that the continuous operation of ultrasonic transducers at high performance levels, particularly in explosion-protected design or for types to be used in moist ambient surroundings, cannot be ensured without major expenditure and/or without a worsening of the efficiency.

The task assignment of the invention is to develop an arrangement for heat discharge, particularly for ultrasonic transducers with high performance ratings which reliably warrants the continuous operation of the ultrasonic transducer, with high performance, also in ambient surroundings with high moisture levels and/or heat and in an explosion-protected design by means of a more effective heat withdrawal that has been known up to the present.

The solution to this task assignment results from the features of claim 1. By means of the closed cooling system enclosing the ultrasonic transducer, this said cooling system consisting of a thin vibration-absorbing elastic layer such as silicone caoutschouc and a heat discharging layer such as quartz sand, a status is achieved where no mechanical losses occur during the transfer of heat capacity because the vibration-absorbing layer does not transfer any vibrations to the following layers. The direct application of the layers onto the ultrasonic transducer produces an effective large-surface heat discharge without having considerably complex equipment which is susceptible to disturbances at the same time.

Purposeful developments of the invention are stated in the Subclaims.

Figure 2:
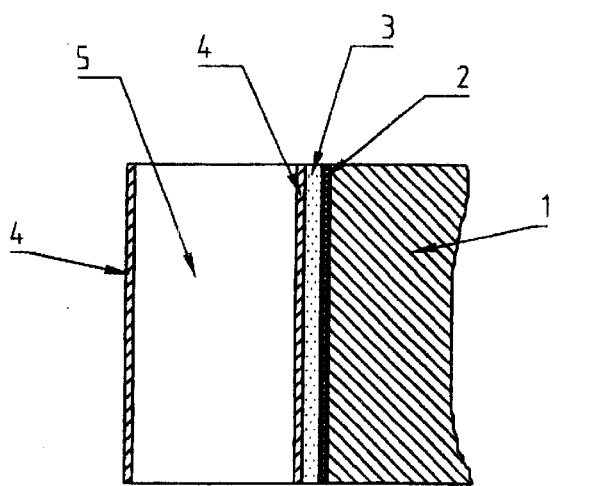

The invention is explained in greater detail in an embodiment of an arrangement for heat discharge for an ultrasonic transducer as shown on a drawing. The following items are shown:

FIG. 1: a schematic cross-sectional illustration of the ultrasonic transducer with cooling system, and FIG. 2: the section A—A through the ultrasonic transducer according to FIG. 1.

For high-performance ultrasonic transducers in the kW-range, the heat discharge is of great significance in order to ensure safe and reliable continuous operation in industrial plants.

From the sectional view in FIG. 1 and the detail illustration in FIG. 2, the arrangement of the cooling system for an ultrasonic transducer is recognisable.

The surface of the ultrasonic transducer 1 is coated with an elastic vibration-absorbing layer 2, for example of silicone caoutschouc, in a layer thickness of 0.05 mm to 0.5 mm for example.

This layer 2 picks up the vibrations radiated from the ultrasonic transducer and absorbs them in such a way that no vibrations occur on the surface of the layer 2.

A heat-conducting layer 3 is applied to layer 2. This heat-conducting layer 3 can consist of quartz sand for example and can have, for example, a thickness of between 0.2 and 2 mm. The heating of the ultrasonic transducer 1 is discharged by way of its entire surface to layer 2 and from there it is discharged to layer 3.

The heat-conducting layer 3 is again joined in close contact with a casing 4, for example of aluminium continuous casting, which can have cooling fins and an external enclosure. Heat-conducting media such as air, water or oil or similar substances can be located between the cooling fins.

In addition, it is also possible to withdraw heat from layer 3 in the known manner by means of ventilation or by means of any other known cooling systems.

The invention is not limited to the embodiments described here. Moreover, it is possible to realise further embodiments by means of a combination of the features without departing from the framework of the invention.

SUMMARY

The invention refers to an arrangement for heat discharge, particularly for ultrasonic transducers with high performance rating for the industrial application.

The task assignment of the invention, to develop a category-related arrangement which warrants the continuous operation of ultrasonic transducers with high performance ratings also in surroundings with high moisture and/or heat levels and in explosion-protected design by means of a more effective heat discharge than known up to the present, is solved in such a way that the ultrasonic transducer 1 is surrounded by a closed cooling system which has a vibration-absorbing layer 2 such as silicone caoutschouc and a heat-withdrawing layer 3 such as quartz sand.

What is claimed is:

1. Arrangement for heat discharge for ultrasonic transducers wherein, a vibration-absorbing elastic layer, that is in direct contact with the surface of the ultrasonic transducer, and a heat discharging layer of a particle-spreadable material, that is in direct contact with the elastic layer, form a cooling system that surrounds the transducer to be cooled.

2. Arrangement according to claim 1, wherein, the heat discharging layer, that is in direct contact with the elastic layer, is joined in close contact with a casing for wide surface discharge of the heat to the outside.

* * * * *

UNITED STATES PATENT AND TRADEMARK OFFICE
CERTIFICATE OF CORRECTION

PATENT NO. : 6,481,493 B1 Page 1 of 1
DATED : November 19, 2002
INVENTOR(S) : Harald Hielscher It is certified that error appears in the above-identified patent and that said Letters Patent is hereby corrected as shown below:

<u>Title page, Item [54] and Column 1, lines 1-4,</u>
Please correct the title from: "ARRANGEMENT FOR HEAT DISCHARGE, PARTICULARLY FOR ULTRASONIC TRANSDUCERS WITH HIGH PERFORMANCE" to -- ARRANGEMENT FOR HEAT DISCHARGE, PARTICULARLY FOR ULTRASONIC TRANSDUCERS WITH HIGH PERFORMANCE RATING--.

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

| | |
|---|---|
| PATENT NO. | : 6,481,493 B1 |
| APPLICATION NO. | : 09/762103 |
| DATED | : November 19, 2002 |
| INVENTOR(S) | : Harald Hielscher |

It is certified that error appears in the above-identified patent and that said Letters Patent is hereby corrected as shown below:

Title Page In item "(73)" please correct the Assignee name from "Dr. Heilscher GmbH, Teltow (DE)" to --Dr. Hielscher GmbH, Teltow (DE)--.

Signed and Sealed this

Twenty-ninth Day of May, 2007

JON W. DUDAS
*Director of the United States Patent and Trademark Office*